US012725060B2

(12) United States Patent
Huang et al.

(10) Patent No.: US 12,725,060 B2
(45) Date of Patent: Sep. 1, 2026

(54) METHOD AND COMPUTING DEVICE OF ESTABLISHING PREDICTION MODEL FOR PREDICTING PROBABILITY OF SUBJECT EXPERIENCING WHITE COAT EFFECT

(71) Applicant: TAIPEI VETERANS GENERAL HOSPITAL, Taipei City (TW)

(72) Inventors: Chin-Chou Huang, Taipei City (TW); Ming-Hui Hung, Taipei City (TW); Ling-Chieh Shih, Kaohsiung City (TW); Yu-Ching Wang, Taipei City (TW); Han Cheng, New Taipei City (TW); Yu-Chieh Shiao, Taichung City (TW); Yu-Hsuan Tseng, Taipei City (TW)

(73) Assignee: TAIPEI VETERANS GENERAL HOSPITAL, Taipei City (TW)

( * ) Notice: Subject to any disclaimer, the term of this patent is extended or adjusted under 35 U.S.C. 154(b) by 547 days.

(21) Appl. No.: 18/364,263

(22) Filed: Aug. 2, 2023

(65) Prior Publication Data

US 2024/0144056 A1 May 2, 2024

Related U.S. Application Data

(60) Provisional application No. 63/427,188, filed on Nov. 22, 2022, provisional application No. 63/420,811, filed on Oct. 31, 2022.

(51) Int. Cl.
*G06N 5/045* (2023.01)
*G06N 5/022* (2023.01)
*G16H 50/30* (2018.01)

(52) U.S. Cl.
CPC ............ *G06N 5/045* (2013.01); *G06N 5/022* (2013.01); *G16H 50/30* (2018.01)

(58) Field of Classification Search
CPC ............................... G06N 5/045; G06N 5/022
See application file for complete search history.

(56) References Cited

U.S. PATENT DOCUMENTS

2022/0156519 A1* 5/2022 Ghorbani ............... G06N 3/091
2022/0188701 A1* 6/2022 Röder .................... G16H 10/60
(Continued)

OTHER PUBLICATIONS

Guimarães et al., "Risk prediction with office and ambulatory blood pressure using artificial intelligence," medRxiv, Jan. 2020, pp. 1-32.
(Continued)

*Primary Examiner* — Khanh B Pham
(74) *Attorney, Agent, or Firm* — Birch, Stewart, Kolasch & Birch, LLP

(57) ABSTRACT

A method includes: obtaining impact values for characteristic conditions; selecting training data subsets respectively from training data sets according to the impact values; obtaining a candidate model and an evaluation value based on the training data subsets; supplementing the training data subsets according to the impact values; obtaining another candidate model and another evaluation value based on training data subsets thus supplemented; repeating the step of supplementing the training data subset, and the step of obtaining another candidate model and another evaluation value based on the training data subsets thus supplemented; and selecting one of the candidate models as a prediction model based on the evaluation values.

17 Claims, 9 Drawing Sheets

(56) References Cited

U.S. PATENT DOCUMENTS

| | | | | |
|---|---|---|---|---|
| 2023/0069693 | A1* | 3/2023 | Tignanelli | G16H 40/67 |
| 2023/0087336 | A1* | 3/2023 | Hadlock | G06F 11/008<br>714/47.3 |
| 2023/0099880 | A1* | 3/2023 | Getz | G16H 20/00<br>705/2 |
| 2023/0157533 | A1* | 5/2023 | Chang | G16H 50/30<br>705/2 |

OTHER PUBLICATIONS

Taiwanese Search Report for corresponding Taiwanese Application No. 112109189, dated Oct. 6, 2023, with English translation.

* cited by examiner

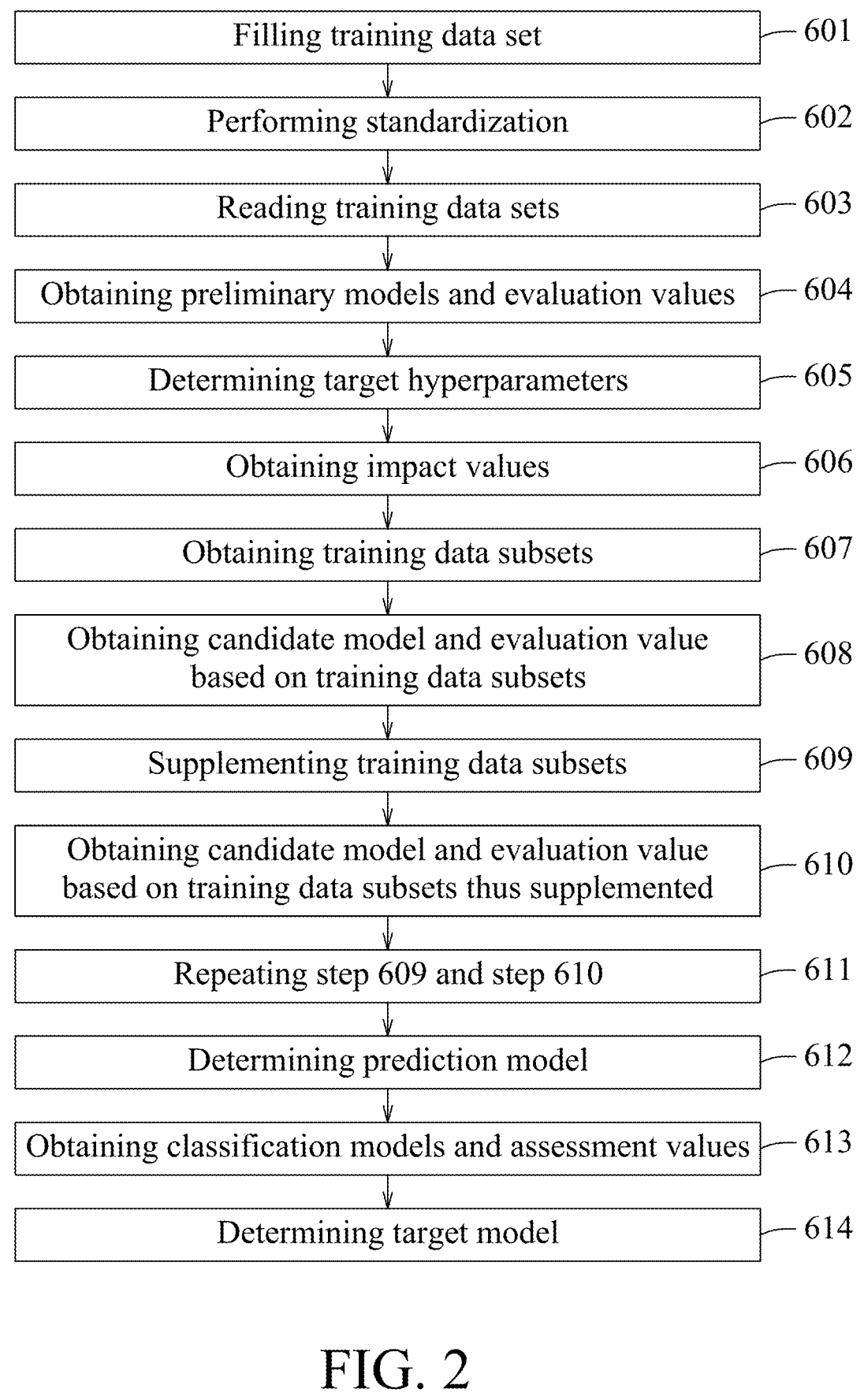

Filling training data set — 601

Performing standardization — 602

Reading training data sets — 603

Obtaining preliminary models and evaluation values — 604

Determining target hyperparameters — 605

Obtaining impact values — 606

Obtaining training data subsets — 607

Obtaining candidate model and evaluation value based on training data subsets — 608

Supplementing training data subsets — 609

Obtaining candidate model and evaluation value based on training data subsets thus supplemented — 610

Repeating step 609 and step 610 — 611

Determining prediction model — 612

Obtaining classification models and assessment values — 613

Determining target model — 614

FIG. 2

Feeding test data set into prediction model to obtain probability of subject experiencing white coat effect

METHOD AND COMPUTING DEVICE OF ESTABLISHING PREDICTION MODEL FOR PREDICTING PROBABILITY OF SUBJECT EXPERIENCING WHITE COAT EFFECT

CROSS-REFERENCE TO RELATED APPLICATION

This application claims the benefit of U.S. Provisional Patent Application Nos. 63/420,811, filed on Oct. 31, 2022, and 63/427,188, filed on Nov. 22, 2022, which is incorporated by reference herein in its entirety.

FIELD

The disclosure relates to a method and a computing device for establishing a prediction model for predicting probability of a subject experiencing white coat effect.

BACKGROUND

A patient who is diagnosed with white-coat hypertension (WCH) or white-coat uncontrolled hypertension (WUCH) would exhibit an elevated blood pressure (BP) level (i.e., systolic/diastolic BP no less than 140/90 mmHg) in a clinical environment (e.g., in a hospital), while the patient would typically exhibit a normal BP level in a non-clinical environment (e.g., at home). More specifically, a patient would be diagnosed with WCH if he/she has not been treated with antihypertensive drug(s) and would be diagnosed with WUCH if he/she has already been treated with antihypertensive drug(s). Studies indicate that approximately 10-30% of patients attending clinics due to high BP experienced WCH or WUCH.

A conventional approach for detecting WCH/WUCH is by using home BP monitoring (HBPM) or 24-hour ambulatory BP monitoring (ABPM). However, such approach is time consuming and labor intensive.

SUMMARY

Therefore, an object of the disclosure is to provide a method and a computing device for establishing a prediction model for predicting probability of a subject experiencing white coat effect that can alleviate at least one of the drawbacks of the prior art.

According to a first aspect of the disclosure, the computing device includes a storage medium and a processor.

The storage medium is configured to store a plurality of original data sets that are respectively related to a plurality of samples and a set of target hyperparameters that is related to a target machine learning algorithm. Each of the original data sets includes a plurality of characteristic parameters respectively related to a plurality of characteristic conditions of the corresponding one of the samples, and a label that indicates whether the corresponding one of the samples experiences white coat effect. The characteristic parameters include a plurality of physiological parameters that are respectively related to a plurality of physiological conditions of the corresponding one of the samples, and a plurality of drug-usage indicators that respectively indicate usage conditions respectively of a plurality of specific drugs by the corresponding one of the samples.

The processor is electrically connected to the storage medium. The processor is configured to obtain, by using the target machine learning algorithm and a model-explanation tool based on the original data sets and the set of target hyperparameters, impact values respectively for the characteristic conditions. Each of the impact values is related to impact of the characteristic parameters that are respectively included in the original data sets and that are related to the corresponding one of the characteristic conditions on an output of a model that is obtained using the target machine learning algorithm. The processor is configured to, for each of the original data sets, select one of the characteristic parameters that is related to one of the characteristic conditions corresponding to a greatest one of the impact values from the original data set as a training data set. The processor is configured to obtain, based on the training data sets and the set of target hyperparameters, a candidate model by using the target machine learning algorithm, and an evaluation value related to the candidate model by using a first validation method. The processor is configured to, for each of the training data sets, supplement the training data set with one of the characteristic parameters that is related to one of the characteristic conditions corresponding to a greatest one of the impact values among the characteristic parameters that are not included in the training data set. The processor is configured to obtain, based on the training data sets thus supplemented and the set of target hyperparameters, another candidate model by using the target machine learning algorithm, and another evaluation value related to said another candidate model by using the first validation method. The processor is configured to repeat supplementing the training data set, and repeat obtaining another candidate model and another evaluation value related to said another candidate model based on the training data sets thus supplemented and the set of target hyperparameters, until the training data sets, each being supplemented to include all of the characteristic parameters, have been used in obtaining another candidate model and another evaluation value. The processor is configured to select, from among the candidate models that are obtained in the obtaining a candidate model and obtaining another candidate model, one of the candidate models as the prediction model based on the evaluation values respectively related to the candidate models.

According to a second aspect of the disclosure, the method is to be implemented by the computing device that is previously described in the first aspect of the disclosure. The method includes steps of: obtaining, by using the target machine learning algorithm and a model-explanation tool based on the original data sets and the set of target hyperparameters, impact values respectively for the characteristic conditions, each of the impact values being related to impact of the characteristic parameters that are respectively included in the original data sets and that are related to the corresponding one of the characteristic conditions on an output of a model that is obtained using the target machine learning algorithm; for each of the original data sets, selecting one of the characteristic parameters that is related to one of the characteristic conditions corresponding to a greatest one of the impact values from the original data set as a training data set; obtaining, based on the training data sets and the set of target hyperparameters, a candidate model by using the target machine learning algorithm, and an evaluation value related to the candidate model by using a first validation method; for each of the training data sets, supplementing the training data set with one of the characteristic parameters that is related to one of the characteristic conditions corresponding to a greatest one of the impact values among the characteristic parameters that are not included in the training data set; obtaining, based on the training data sets thus supplemented and the set of target hyperparameters, another candidate model by using the target machine learning algorithm, and another evaluation value related to said another candidate model by using the first validation method; repeating the step of supplementing the training data set, and the step of obtaining another candidate model and another evaluation value related to said another candidate model based on the training data sets thus supplemented and the set of target hyperparameters, until the training data sets, each being supplemented to include all of the characteristic parameters, have been used in the step of obtaining another candidate model and another evaluation value; and selecting, from among the candidate models that are obtained in the step of obtaining a candidate model and the step of obtaining another candidate model, one of the candidate models as the prediction model based on the evaluation values respectively related to the candidate models.

BRIEF DESCRIPTION OF THE DRAWINGS

Other features and advantages of the disclosure will become apparent in the following detailed description of the embodiment(s) with reference to the accompanying drawings. It is noted that various features may not be drawn to scale.

FIG. 2 is a flow chart illustrating an embodiment of a method of establishing a prediction model for predicting the probability of a subject experiencing WCH or WUCH according to the disclosure.

FIG. 8 is a flow chart illustrating an embodiment of a method for predicting the probability of a subject experiencing WCH or WUCH according to the disclosure.

DETAILED DESCRIPTION

Figure 1:
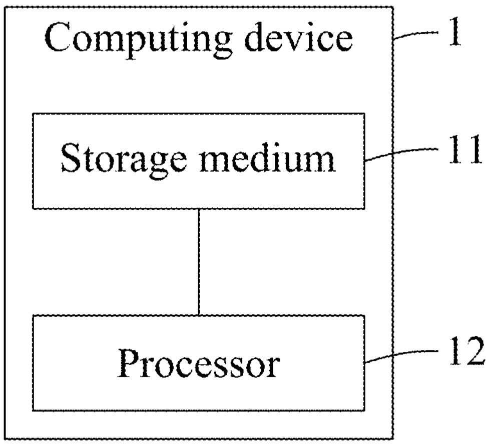
FIG. 1 is a block diagram illustrating an embodiment of a computing device of establishing a prediction model for predicting probability of a subject experiencing white-coat hypertension (WCH) or white-coat uncontrolled hypertension (WUCH) according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Referring to FIG. 1, an embodiment of a computing device 1 for establishing a prediction model for predicting probability of a subject experiencing white coat effect according to the disclosure is illustrated. It should be noted that, throughout this disclosure, the term "white coat effect" means that a person exhibits an elevated office blood pressure, and includes white-coat hypertension (WCH) and white-coat uncontrolled hypertension (WUCH). The computing device 1 may be implemented as a personal computer (PC), a desktop computer, a laptop computer, a notebook computer, a tablet computer, a smartphone or a computing server, but implementation thereof is not limited to what are disclosed herein and may vary in other embodiments.

The computing device 1 includes a storage medium 11, and a processor 12 that is electrically connected to the storage medium 11.

The storage medium 11 may be implemented by random access memory (RAM), double data rate synchronous dynamic random access memory (DDR SDRAM), read only memory (ROM), programmable ROM (PROM), flash memory, a hard disk drive (HDD), a solid state disk (SSD), electrically-erasable programmable read-only memory (EEPROM) or any other volatile/non-volatile memory devices, but is not limited thereto.

The processor 12 may be implemented by a central processing unit (CPU), a microprocessor, a micro control unit (MCU), a system on a chip (SoC), or any circuit configurable/programmable in a software manner and/or hardware manner to implement functionalities discussed in this disclosure.

The storage medium 11 is configured to store a plurality of training data sets that are respectively related to a plurality of human subjects (hereinafter referred to as "samples"), and a set of target hyperparameters that is related to a target machine learning algorithm. Each of the training data sets includes a plurality of characteristic parameters that are respectively related to a plurality of characteristic conditions of the corresponding one of the samples, and a label that indicates whether the corresponding one of the samples have experienced WCH or WUCH. The characteristic parameters include a plurality of physiological parameters that are respectively related to a plurality of physiological conditions of the corresponding one of the samples, and a plurality of drug-usage indicators that respectively indicate usage conditions respectively of a plurality of specific drugs by the corresponding one of the samples. Specifically, the physiological conditions include sex, age, body mass index (BMI), waist-hip ratio (WHR), office systolic blood pressure (BP), office diastolic BP, office pulse pressure, level of total cholesterol (TC), level of triglyceride (TG), level of high-density lipoprotein cholesterol (HDL-C), level of low-density lipoprotein cholesterol (LDL-C), estimated glomerular filtration rate (eGFR), level of creatinine, level of sodium, level of potassium, level of alanine aminotransferase, level of uric acid, level of fasting glucose, current smoking status and level of aldosterone. It is worth to note that each one of the physiological conditions of the office systolic BP, the office diastolic BP and the office pulse pressure may have one or more BP values that are obtained by measuring, one or more times, said one of the physiological conditions of the office systolic BP, the office diastolic BP and the office pulse pressure of the sample. The specific drugs include angiotensin converting enzyme inhibitors/angiotensin receptor blockers (ACEIs/ARBs), beta blockers, calcium channel blockers (CCBs), thiazide, spironolactone, alpha blockers, etc. In this embodiment, in each training data set of a sample, each of the drug-usage indicators has a value of one to indicate that the sample used the corresponding one of the specific drugs, and have a value of zero to indicate that the sample did not use the corresponding one of the specific drugs, but is not limited thereto. The target machine learning algorithm may be random forest (RF) algorithm, an eXtreme Gradient Boosting (XGBoost) algorithm, logistic regression (LR) algorithm, an artificial neural network (ANN) algorithm, a support vector machine (SVM) algorithm, or the like. In a scenario where the target machine learning algorithm is the ANN algorithm, the set of target hyperparameters includes a value (e.g., two or three) that represents a number of hidden layers of an ANN model, and at least one value (e.g., 200 or 250) that represents a number of neurons in each of the hidden layers of the ANN model. For example, the ANN model may have two hidden layers each having 200 neurons, or may have a first hidden layer having 200 neurons and a second hidden layer having 250 neurons, but implementation of the ANN model is not limited thereto.

In one embodiment, for each of the training data sets, the processor 12 is configured to determine whether the training data set is missing a physiological parameter related to one of the physiological conditions, and when it is determined that the training data set is missing a physiological parameter, to fill the training data set with a predetermined parameter related to the one of the physiological conditions. It should be noted that the processor 12 may fill the training data set with a mean of all available physiological parameters related to the one of the physiological conditions in other training data sets, or may fill the training data set by using multiple imputation. However, the way of filling the training data set is not limited to the disclosure herein and may vary in other embodiments. Since implementation of multiple imputation has been well known to one skilled in the relevant art, detailed explanation of the same is omitted herein for the sake of brevity.

In one embodiment, for each of the training data sets, the processor 12 is further configured to perform standardization on each of the physiological parameters such that each of the physiological parameters falls within a numerical interval ranging from −1 to 1. Specifically, for each of the physiological parameters in each of the training data sets, the processor 12 calculates a difference by subtracting from said each of the physiological parameters a mean of all physiological parameters related to the same one of the physiological conditions in all of the training data sets, and divides the difference thus calculated by a standard deviation of all physiological parameters corresponding to said each of the physiological parameters in all of the training data sets. However, the way of performing standardization is not limited to the disclosure herein and may vary in other embodiments.

Figure 3:
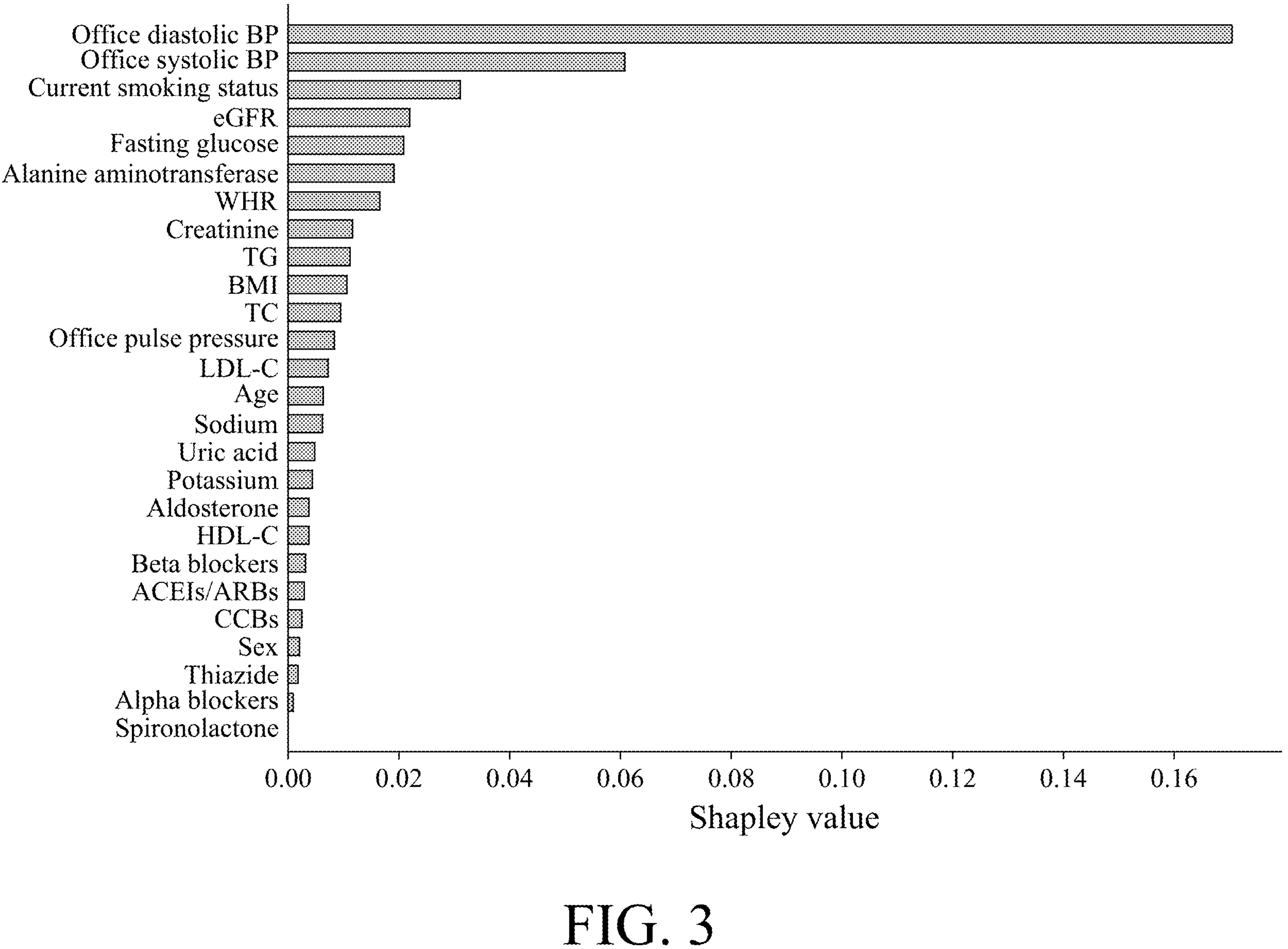
FIG. 3 is a bar chart of impact values respectively for the characteristic conditions.

The processor 12 is further configured to obtain impact values respectively for the characteristic conditions by using the target machine learning algorithm and a model-explanation tool based on the training data sets and the set of target hyperparameters. Each of the impact values is related to the impact of the characteristic parameters that are respectively included in the training data sets and that are related to the corresponding one of the characteristic conditions on an output of a model that is obtained using the target machine learning algorithm. Particularly, the model-explanation tool is SHapley Additive exPlanations (SNAP), and each of the impact values is a Shapley value. Referring to FIG. 3, a bar chart of impact values respectively for the characteristic parameters is exemplarily illustrated.

For each of the training data sets, the processor 12 is configured to select one of the characteristic parameters that is related to one of the characteristic conditions corresponding to a greatest one of the impact values from the training data set as a training data subset. Based on the training data subsets and the set of target hyperparameters, the processor 12 is further configured to obtain a candidate model by using the target machine learning algorithm, and to obtain an evaluation value related to the candidate model by using a first validation method. The first validation method involves k-fold cross-validation (where k is a positive integer, e.g., five) and calculation of an area under the receiver operating characteristic curve (AUROC), but is not limited thereto. For example, in other embodiments, the first validation method involves k-fold cross-validation and determining one of an area under the precision-recall curve, an F1 score, an F2 score, sensitivity, specificity, a positive predictive value (PPV), a negative predictive value, and a calibration-in-the-large and a calibration slope in a calibration plot. Since the aforesaid statistical analysis has been well known to one skilled in the relevant art, detailed explanation of the same is omitted herein for the sake of brevity.

For explanation, in a scenario where 5-fold cross-validation and calculation of the AUROC are used, the training data subsets are evenly divided into first to fifth groups in a manner that each of the first to fifth groups includes an identical number of the training data subsets. Firstly, the first to fourth groups are used to train the candidate model by using the target machine learning algorithm, and the fifth group is used to obtain a first AUROC that is related to the candidate model thus trained. Secondly, the second to fifth groups are used to train the candidate model by using the target machine learning algorithm, and the first group is used to obtain a second AUROC that is related to the candidate model thus trained. Thirdly, the first, and third to fifth groups are used to train the candidate model by using the target machine learning algorithm, and the second group is used to obtain a third AUROC that is related to the candidate model thus trained. Fourthly, the first, second, fourth and fifth groups are used to train the candidate model by using the target machine learning algorithm, and the third group is used to obtain a fourth AUROC that is related to the candidate model thus trained. Fifthly, the first to third, and fifth groups are used to train the candidate model by using the target machine learning algorithm, and the fourth group is used to obtain a fifth AUROC that is related to the candidate model thus trained. Finally, the processor 12 calculates an average of the first to fifth AUROCs as the evaluation value. It is worth to note that in this embodiment, the greater the evaluation value, the better the candidate model.

For each of the training data subsets, the processor 12 is further configured to supplement the training data subset with one of the characteristic parameters that is related to one of the characteristic conditions corresponding to a greatest one of the impact values among the characteristic parameters that are not included in the training data subset. Next, the processor 12 is further configured to obtain, based on the training data subsets thus supplemented and the set of target hyperparameters, another candidate model by using the target machine learning algorithm, and another evaluation value related to said another candidate model by using the first validation method. The processor 12 is configured to repeat supplementing the training data subset, and to repeat obtaining another candidate model and another evaluation value related to said another candidate model based on the training data subsets thus supplemented and the set of target hyperparameters, until the training data subsets, each being supplemented to include all of the characteristic parameters, have all been used in obtaining another candidate model and another evaluation value. Subsequently, the processor 12 is configured to select, from among the candidate models thus obtained, one of the candidate models as the prediction model based on the evaluation values respectively related to the candidate models. In particular, the processor 12 is configured to select one of the candidate models that corresponds to a greatest one of the evaluation values as the prediction model. In this way, prediction accuracy of the prediction model may be ensured.

For explanation, in a scenario where the impact value (i.e., the Shapley value) for the physiological condition of the office diastolic BP is a greatest one among the impact values respectively for the characteristic conditions (which are 26 in number) as shown in FIG. 3, the processor 12 selects, for each of the training data sets, one of the characteristic parameters that is related to the physiological condition of the office diastolic BP from the training data set as a training data subset, and obtains a first candidate model and a first evaluation value based on the training data subsets. After the first candidate model and the first evaluation value have been obtained, the processor 12 supplements each of the training data subsets by supplementing the same with one of the characteristic parameters that is related to the physiological condition of the office systolic BP, wherein the impact value for the physiological condition of the office systolic BP is a greatest one among the impact values respectively for the 25 characteristic parameters. Subsequently, the processor 12 obtains a second candidate model and a second evaluation value based on the training data subsets thus supplemented. It is worth to note that each of the training data subsets has been supplemented with the characteristic parameter that is related to the physiological condition of the office systolic BP, and thereby includes two characteristic parameters. Then, the processor 12 supplements each of the training data subsets by supplementing the same with one of the characteristic parameters that is related to the physiological condition of the current smoking status, wherein the impact value for the physiological condition of the current smoking status is a greatest one among the impact values respectively for the 24 characteristic parameters. Subsequently, the processor 12 obtains a third candidate model and a third evaluation value based on the training data subsets thus supplemented, and now each of the training data subsets includes three characteristic parameters. Likewise, similar procedures are repeated, until each of the training data subsets has been supplemented to include all of the characteristic parameters and has been used to obtain a $26^{th}$ candidate model and a $26^{th}$ evaluation value.

In order to predict the probability of a subject experiencing WCH/WUCH, the processor 12 is further configured to receive a test data set that is related to the subject, wherein the test data set includes at least one characteristic parameter that is related to one of the physiological conditions and the usage conditions of the subject. In this embodiment, the test data set includes characteristic parameters that are related to all of the aforementioned physiological conditions and the aforementioned usage conditions of the subject. It should be noted that the test data set at least includes the characteristic parameter(s) related to the characteristic conditions(s) that is/are identical to the characteristic conditions(s) of all characteristic parameter(s) in each of the training data subsets that are used to obtain the prediction model. In one embodiment, the test data set includes physiological parameter(s) that are only related to the physiological condition(s) of the subject. In one embodiment, the test data set includes drug-usage indicator(s) that are only related to the usage condition(s) of the subject. Next, the processor 12 is further configured to feed the test data set into the prediction model to obtain the probability of the subject experiencing WCH/WUCH.

In the case where the RF algorithm is used to obtain the prediction model, the test data set may include physiological parameters that are respectively related to the office systolic BP, the office diastolic BP, the eGFR, the level of fasting glucose and the current smoking status of the subject.

In the case where the XGBoost algorithm is used to obtain the prediction model, the test data set may include a drug-usage indicator indicating the usage condition of CCBs by the subject, and physiological parameters that are respectively related to the office systolic BP, the office diastolic BP, the eGFR, the WHR, the level of creatinine, the level of TG, the level of fasting glucose, the level of alanine aminotransferase, the level of sodium, the level of potassium, the BMI and the current smoking status of the subject.

In the case where the LR algorithm is used to obtain the prediction model, the test data set may include a drug-usage indicator indicating the usage condition of beta blockers by the subject, and physiological parameters that are respectively related to the office systolic BP, the office diastolic BP, the eGFR, the WHR, the level of TG, the BMI, the level of TC, the level of uric acid, the level of HDL-C, the level of potassium and the current smoking status of the subject.

In the case where the ANN algorithm is used to obtain the prediction model, the test data set may include physiological parameters that are respectively related to the office systolic BP, the office diastolic BP, the eGFR, the WHR, the level of potassium and the level of TG.

In one embodiment, the storage medium 11 is further configured to store a plurality of sets of candidate hyperparameters that are respectively related to a plurality of candidate machine learning algorithms. That is to say, each of the sets of candidate hyperparameters corresponds to a respective one of the candidate machine learning algorithms. For each of the sets of candidate hyperparameters, the processor 12 is further configured to obtain, based on the training data sets and the set of candidate hyperparameters, a preliminary model by using the corresponding one of the candidate machine learning algorithms, and an evaluation value related to the preliminary model by using a second validation method. Accordingly, a plurality of preliminary models corresponding respectively to the candidate machine learning algorithms are obtained, and a plurality of evaluation values related respectively to the preliminary models are obtained as well. Then, the processor 12 is further configured to select, from among the candidate machine learning algorithms, one of the candidate machine learning algorithms that is used to obtain the preliminary model having a greatest one of the evaluation values as the target machine learning algorithm, and to select from among the sets of candidate hyperparameters, one of the sets of candidate hyperparameters that is related to the selected one of the candidate machine learning algorithms as the set of target hyperparameters. Next, the processor 12 is further configured to store the target machine learning algorithm and the set of target hyperparameters in the storage medium 11. In this embodiment, the candidate machine learning algorithms includes the SVM algorithm, the RF algorithm, the XGBoost algorithm, the LR algorithm, and the ANN algorithm; the second validation method involves the k-fold cross-validation and the calculation of AUROC, but is not limited thereto.

In one embodiment, the storage medium 11 is further configured to store a plurality of classification thresholds that are related to the target machine learning algorithm. For each of the classification thresholds, the processor 12 is further configured to obtain, based on the set of target hyperparameters and the training data subsets that are used to obtain the prediction model, a classification model by using the target machine learning algorithm, and an assessment value related to the classification model by using a third validation method. Specifically, for each of the classification thresholds, the processor 12 obtains the classification model by adjusting weightings of the prediction model based on comparison of the classification threshold and output of the prediction model. Then, the processor 12 is further configured to select, from among the classification models thus obtained, one of the classification models that corresponds to a greatest one of the assessment values respectively related to the classification models as a target model for determining whether or not the subject experiences WCH/WUCH. In this embodiment, the third validation method involves the k-fold cross-validation and determination of F1 score, but is not limited thereto. Specifically, for each of the classification thresholds, the processors 12 calculates a mean of k number of F1 scores as the assessment value that is related to the classification model. It is worth to note that the greater the assessment value, the better the classification model.

In four different cases, the processor 12 obtains four target models by respectively using the RF algorithm, the ANN algorithm, the XGBoost algorithm and the LR algorithm. In each of the four different cases, the processor 12 determines a receiver operating characteristic (ROC) curve that is related to the target model based on internal validation data that is related to patients with hypertension and that is collected from six medical centers in Taiwan, and presents the ROC curve as a visual output (e.g., presenting the ROC curve by a display). In addition, in each of the four different cases, the processor 12 determines another ROC curve that is related to the target model based on external validation data that is related to patients with hypertension and that is collected from Taipei Veterans General Hospital in Taiwan, and presents the another ROC curve as another visual output. In this way, performance of the four classification models can be further analyzed.

Figure 4:
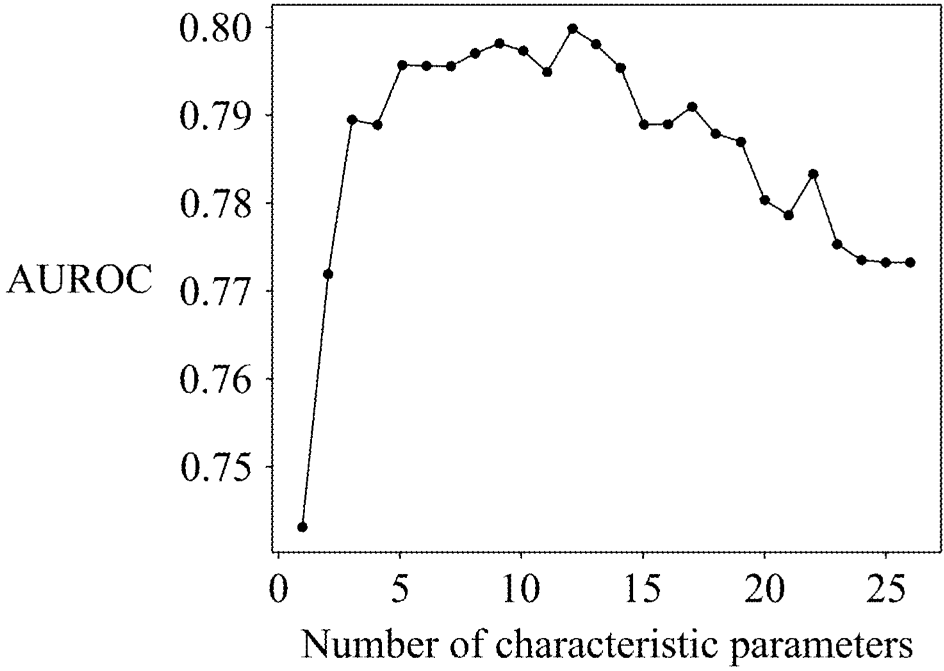
FIGS. 4-7 are four line charts, respectively for four machine learning algorithms, of area under the receiver operating characteristic curve (AUROC) versus a number of the characteristic parameters.
Figure 5:
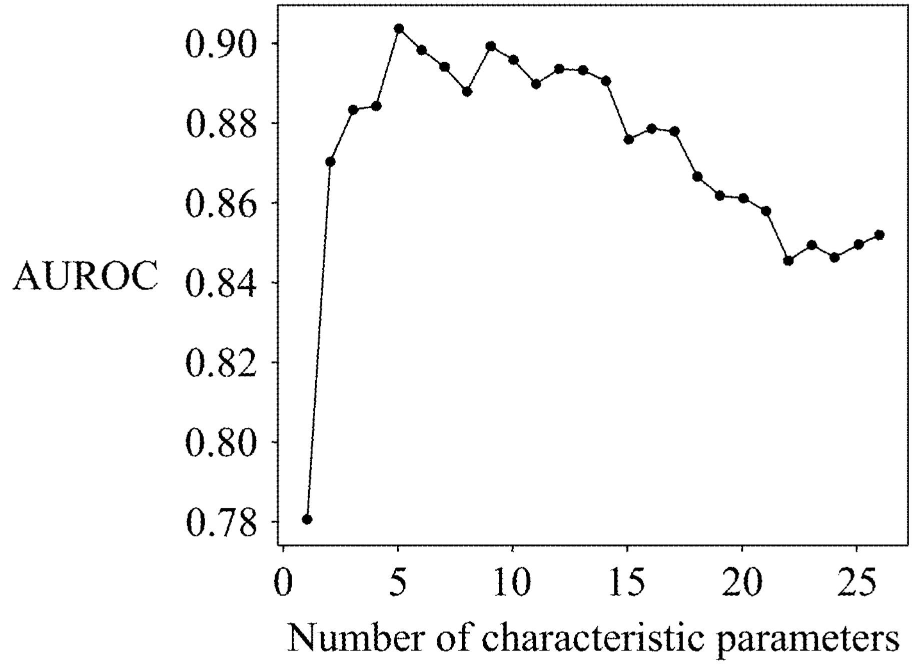
Figure 6:
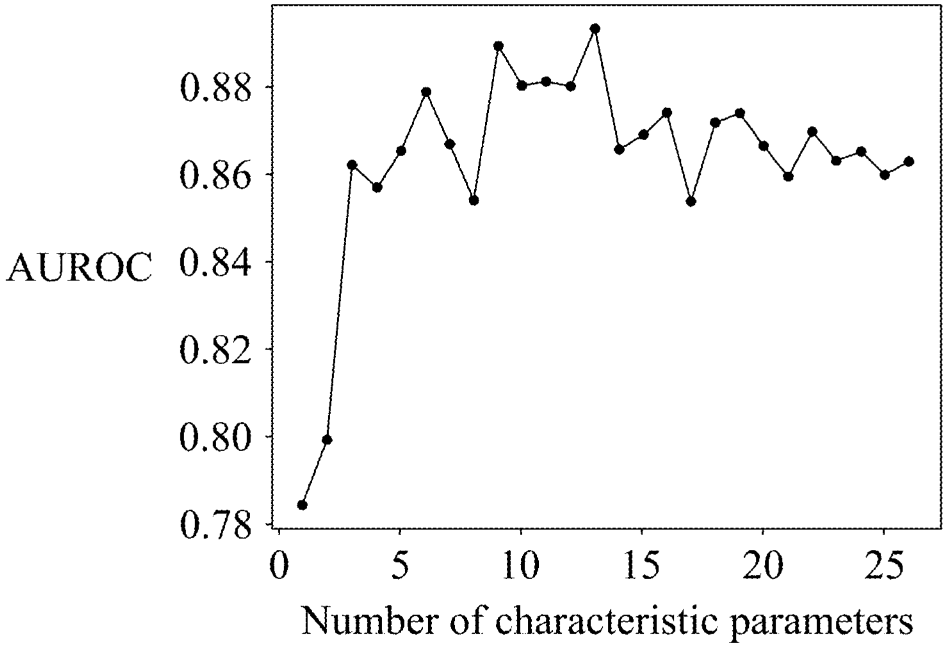
Figure 7:
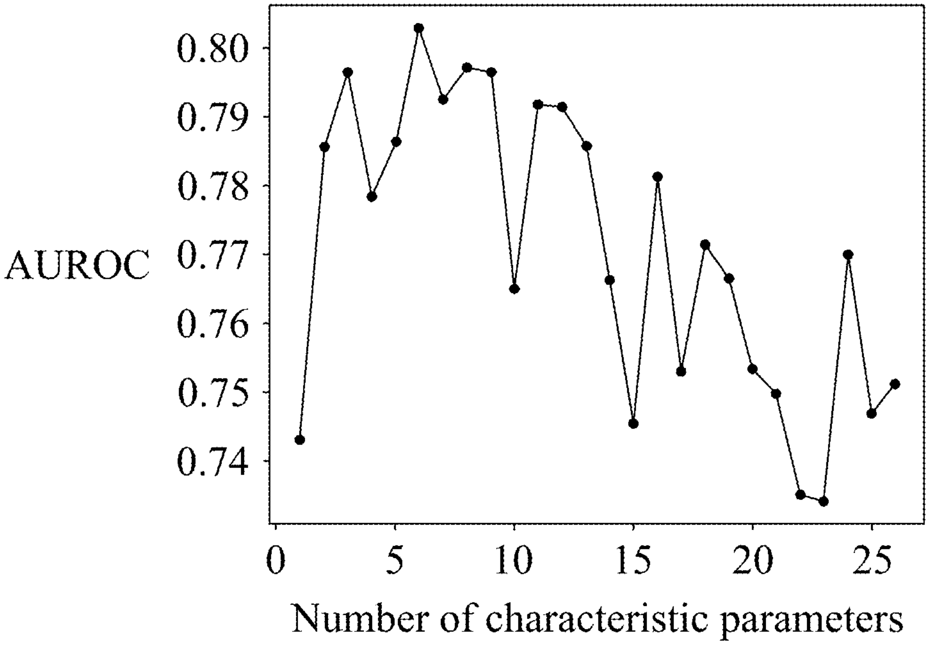

FIGS. 4-7 illustrate, respectively for four machine learning algorithms, four line charts of AUROC versus a number of characteristic parameters. FIG. 4 corresponds to the LR algorithm; FIG. 5 corresponds to the RF algorithm; FIG. 6 corresponds to the XGBoost algorithm; FIG. 7 corresponds to the ANN algorithm. For each of the four line charts, a vertical axis corresponds to an AUROC ranging from 0 to 1, and a horizontal axis corresponds to a number of characteristic parameters ranging from 1 to 26.

Referring to FIG. 2, an embodiment of a method of establishing a prediction model for predicting the probability of a subject experiencing WCH/WUCH according to the disclosure is illustrated. The method is implemented by the computing device 1 that is previously described. The method includes steps 601 to 614 delineated below. It is worth to note that steps 601 and 602 belong to stage 1 for preprocessing the training data sets; steps 603 to 605 belong to stage 2 for selecting the target machine learning algorithm (i.e., selecting the set of target hyperparameters); step 606 belongs to stage 3 for obtaining the impact values; steps 607 to 612 belong to stage 4 for obtaining the prediction model; steps 613 and 614 belong to stage 5 for obtaining the target model.

In step 601, for each of the training data sets, the processor 12 of the computing device 1 determines whether the training data set is missing a physiological parameter related to one of the physiological conditions, and when it is determined that the training data set is missing a physiological parameter, fills the training data set with a predetermined parameter related to the one of the physiological conditions.

In step 602, for each of the training data sets, the processor 12 performs standardization on each of the physiological parameters in the training data set. The training data sets that have been processed in steps 601 and 602 of stage 1 will be stored in the storage medium 11 of the computing device 1.

In step 603, the processor 12 reads the training data sets that have been processed and stored in stage 1 from the storage medium 11 of the computing device 1.

In step 604, for each of the sets of candidate hyperparameters, the processor 12 obtains, by using the corresponding one of the candidate machine learning algorithms and the second validation method based on the training data sets and the set of candidate hyperparameters, the preliminary model and the evaluation value related to the preliminary model.

In step 605, the processor 12 selects, from among the sets of candidate hyperparameters, one of the sets of candidate hyperparameters that corresponds to a greatest one of the evaluation values obtained in step 604 as the set of target hyperparameters. Then, the processor 12 stores the set of target hyperparameters in the storage medium 11.

In step 606, the processor 12 obtains, by using the target machine learning algorithm and the model-explanation tool based on the training data sets and the set of target hyperparameters, the impact values that respectively indicate impact of the characteristic parameters on an output of a model that is obtained using the target machine learning algorithm.

In step 607, for each of the training data sets, the processor 12 selects one of the characteristic parameters that is related to one of the characteristic conditions corresponding to a greatest one of the impact values from the training data set as a training data subset.

In step 608, the processor 12 obtains, based on the training data subsets and the set of target hyperparameters, a candidate model by using the target machine learning algorithm, and an evaluation value related to the candidate model by using the first validation method.

In step 609, for each of the training data subsets, the processor 12 supplements the training data subset with one of the characteristic parameters that is related to one of the characteristic conditions corresponding to a greatest one of the impact values among the characteristic parameters that are not included in the training data subset.

In step 610, the processor 12 obtains, based on the training data subsets thus supplemented in step 609 and the set of target hyperparameters, another candidate model by using the target machine learning algorithm, and another evaluation value related to said another candidate model by using the first validation method.

In step 611, the processor 12 repeats step 609 of supplementing the training data subset, and repeats step 610 of obtaining another candidate model and another evaluation value related to said another candidate model based on the training data subsets thus supplemented in step 609 and the set of target hyperparameters, until the training data subsets, each being supplemented to include all of the characteristic parameters, have been used in step 610 of obtaining another candidate model and another evaluation value.

In step 612, the processor 12 selects, from among the candidate models that are obtained in steps 608 and 610, one of the candidate models as the prediction model based on the evaluation values respectively related to the candidate models. Specifically, the processor 12 selects one of the candidate models that corresponds to a greatest one of the evaluation values as the prediction model. The prediction model and the training data sets that are used to obtain the prediction model will be stored in the storage medium 11.

In step 613, the processor 12 reads the training data sets that are used to obtain the prediction model. Thereafter, for each of the classification thresholds, the processor 12 obtains, based on the set of target hyperparameters and the training data subsets that are used to obtain the prediction model, a classification model by using the target machine learning algorithm, and the assessment value related to the classification model by using the third validation method.

In step 614, the processor 12 selects, from among the classification models obtained in step 612, one of the classification models that corresponds to a greatest one of the assessment values respectively related to the classification models as the target model for determining whether or not the subject experiences WCH/WUCH.

Figure 8:
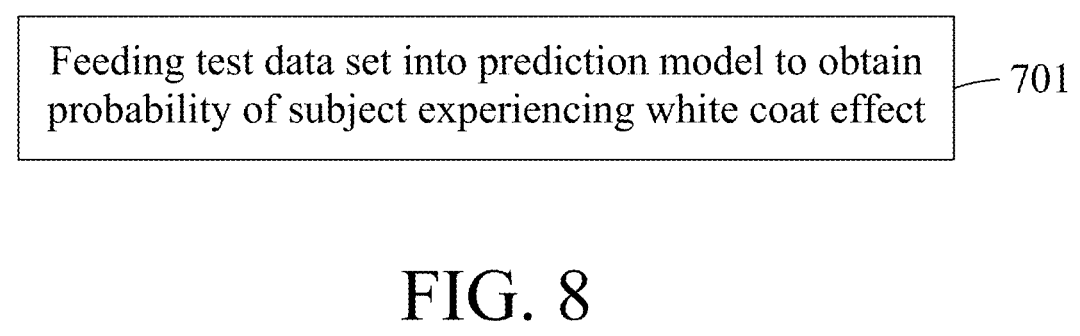

Referring to FIG. 8, an embodiment of a method for predicting the probability of a subject experiencing WCH/WUCH according to the disclosure is illustrated. The method is implemented by the computing device 1 and the prediction model that are previously described. The method includes step 701 described as follows.

In step 701, the processor 12 of the computing device 1 receives a test data set that is related to the subject and that is exemplarily generated based on user operation performed on an input device (e.g., a keyboard, not shown) of the computing device 1. The test data set includes at least one characteristic parameter that is related to one of the physiological conditions and the usage conditions of the subject. Then, the processor 12 feeds the test data set into the prediction model to obtain the probability of the subject experiencing WCH/WUCH. In one embodiment, the processor 12 further feeds the test data set into the target model to determine whether or not the subject experienced WCH/WUCH.

In one embodiment, there is provided a non-transitory machine readable storage medium storing program instructions, when being executed by a processor, causing the processor to implement the target model that is obtained by the method according to the disclosure. The non-transitory machine readable storage medium may be implemented by read only memory (ROM), random access memory (RAM), magnetic disk storage media (e.g., hard disk drive), optical storage media (e.g., compact disc (CD), Digital Versatile Disc (DVD), Blu-ray Disc or the like), flash memory devices (e.g., solid-state drive), etc., but is not limited thereto. The processor may be implemented by a central processing unit (CPU), a microprocessor, a micro control unit (MCU), a system on a chip (SoC), or any circuit configurable/programmable in a software manner and/or hardware manner to implement functionalities discussed in this disclosure.

In one embodiment, there is provided a computer program product embodied on a non-transitory machine readable storage for implementing a method of determining whether a subject experienced white coat effect. The method of determining whether a subject experienced white coat effect includes receiving a test data set that is related to the subject, wherein the test data set includes at least one characteristic parameter that is related to one of a physiological condition of the subject and a usage condition of a specific drug by the subject. The method of determining whether a subject experienced white coat effect further includes feeding the test data set into the target model that is previously described in the foregoing embodiments to determine whether or not the subject experienced white coat effect (WCH/WUCH).

Figure 9:
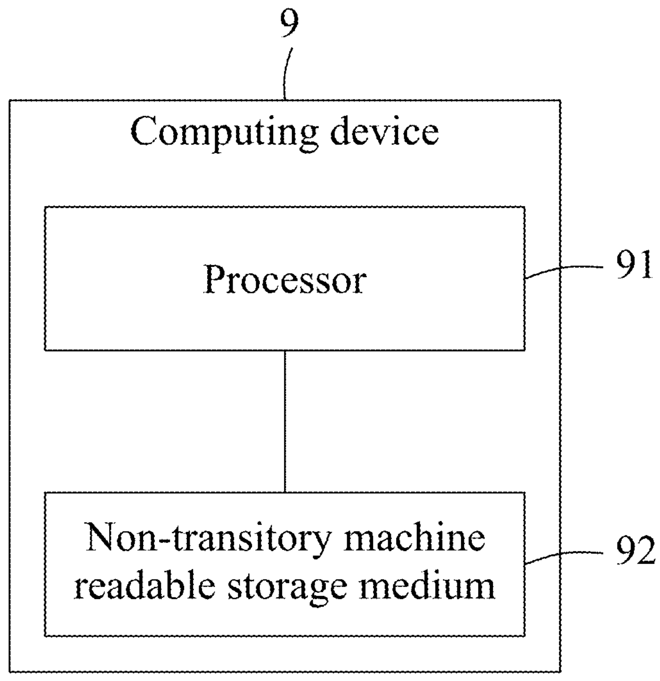
FIG. 9 is a block diagram illustrating an embodiment of a computing device for determining whether a subject experienced white coat effect or not according to the disclosure.

Referring to FIG. 9, an embodiment of a computing device 9 for determining whether a subject has experienced white coat effect (WCH/WUCH) or not is illustrated. The computing device 9 includes a processor 91, and a non-transitory machine readable storage medium 92 that is electrically connected to the processor 91. The non-transitory machine readable storage medium 92 stores program instructions, when being executed by the processor 91, causing the processor 91 to receive a test data set that is related to a subject and to feed the test data set into the target model that is previously described in the foregoing embodiments to determine whether or not the subject experienced WCH/WUCH. The computing device 9 may be implemented by a smart phone, a desktop computer, a tablet computer, a laptop computer, a sphygmomanometer (i.e., a blood pressure meter), a wearable device (e.g., a wearable sphygmomanometer), or any electronic device that is capable of storing and executing application software, but is not limited thereto. The non-transitory machine readable storage medium 92 may be implemented by read only memory (ROM), random access memory (RAM), magnetic disk storage media (e.g., hard disk drive), optical storage media (e.g., compact disc (CD), Digital Versatile Disc (DVD), Blu-ray Disc or the like), flash memory devices (e.g., solid-state drive), etc., but is not limited thereto. The processor 91 may be implemented by a central processing unit (CPU), a microprocessor, a micro control unit (MCU), a system on a chip (SoC), or any circuit configurable/programmable in a software manner and/or hardware manner to implement functionalities discussed in this disclosure.

To sum up, for the method and the computing device 1 of establishing a prediction model for predicting the probability of a subject experiencing WCH/WUCH according to the disclosure, the processor 12 determines the impact values (i.e., the Shapley values) respectively for the characteristic conditions, and generates the candidate models and the evaluation values respectively for the candidate models with the training data subsets that may be supplemented according to the impact values. Subsequently, the processor 12 selects one of the candidate models as the prediction model based on the evaluation values. The prediction model can be used to predict the probability of a subject experiencing WCH/WUCH by feeding into the prediction model a test data set that is related to the subject. In this way, the probability of a subject experiencing WCH/WUCH can be conveniently and efficiently determined.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects; such does not mean that every one of these features needs to be practiced with the presence of all the other features. In other words, in any described embodiment, when implementation of one or more features or specific details does not affect implementation of another one or more features or specific details, said one or more features may be singled out and practiced alone without said another one or more features or specific details. It should be further noted that one or more features or specific details from one embodiment may be practiced together with one or more features or specific details from another embodiment, where appropriate, in the practice of the disclosure.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A method of establishing a prediction model for predicting probability of a subject experiencing white coat effect, to be implemented by a computing device, the computing device storing a plurality of training data sets that are respectively related to a plurality of samples, a set of target hyperparameters that is related to a target machine learning algorithm and a plurality of classification thresholds that are related to the target machine learning algorithm, each of the training data sets including a plurality of characteristic parameters respectively related to a plurality of characteristic conditions of the corresponding one of the samples, and a label that indicates whether the corresponding one of the samples experiences white coat effect, the characteristic parameters including a plurality of physiological parameters that are respectively related to a plurality of physiological conditions of the corresponding one of the samples, and a plurality of drug-usage indicators that respectively indicate usage conditions respectively of a plurality of specific drugs by the corresponding one of the samples, the method comprising steps of:

obtaining, by using the target machine learning algorithm and a model-explanation tool based on the training data sets and the set of target hyperparameters, impact values respectively for the characteristic conditions, each of the impact values being related to impact of the characteristic parameters that are respectively included in the training data sets and that are related to the corresponding one of the characteristic conditions on an output of a model that is obtained using the target machine learning algorithm;

for each of the training data sets, selecting one of the characteristic parameters that is related to one of the characteristic conditions corresponding to a greatest one of the impact values from the training data set as a training data subset;

obtaining, based on the training data subsets and the set of target hyperparameters, a candidate model by using the target machine learning algorithm, and an evaluation value related to the candidate model by using a first validation method;

for each of the training data subsets, supplementing the training data subset with one of the characteristic parameters that is related to one of the characteristic conditions corresponding to a greatest one of the impact values among the characteristic parameters that are not included in the training data subset;

obtaining, based on the training data subsets thus supplemented and the set of target hyperparameters, another candidate model by using the target machine learning algorithm, and another evaluation value related to said another candidate model by using the first validation method;

repeating the step of supplementing the training data subset, and the step of obtaining another candidate model and another evaluation value related to said another candidate model based on the training data subsets thus supplemented and the set of target hyperparameters, until the training data subsets, each being supplemented to include all of the characteristic parameters, have been used in the step of obtaining another candidate model and another evaluation value; and selecting, from among the candidate models that are obtained in the step of obtaining a candidate model and the step of obtaining another candidate model, one of the candidate models as the prediction model based on the evaluation values respectively related to the candidate models, the method further comprising steps, subsequent to the step of obtaining the prediction model, of:

for each of the classification thresholds, obtaining based on the set of target hyperparameters and the training data subsets that are used to obtain the prediction model, a classification model by using the target machine learning algorithm, and an assessment value related to the classification model by using a third validation method; and selecting, from among the classification models thus obtained, one of the classification models that corresponds to a greatest one of the assessment values respectively related to the classification models as a target model for determining whether or not the subject experiences white coat effect.

2. The method as claimed in claim 1, wherein the model-explanation tool is SHapley Additive explanations (SHAP), and each of the impact values is a Shapley value.

3. The method as claimed in claim 1, prior to the step of obtaining impact values, the method further comprising steps, for each of the training data sets, of:

determining whether the training data set is missing a physiological parameter related to one of the physiological conditions;

when it is determined that the training data set is missing a physiological parameter, filling the training data set with a predetermined parameter related to the one of the physiological conditions; and performing standardization on each of the physiological parameters.

4. The method as claimed in claim 1, wherein the step of selecting one of the candidate models as the prediction model is to select one of the candidate models that corresponds to a greatest one of the evaluation values as the prediction model.

5. The method as claimed in claim 1, the computing device further storing a plurality of sets of candidate hyperparameters that are respectively related to a plurality of candidate machine learning algorithms, the method further comprising steps, prior to the step of obtaining impact values, of:

for each of the sets of candidate hyperparameters, obtaining, based on the training data sets and the set of candidate hyperparameters, a preliminary model by using the corresponding one of the candidate machine learning algorithms, and an evaluation value related to the preliminary model by using a second validation method; and selecting, from among the sets of candidate hyperparameters, one of the sets of candidate hyperparameters that corresponds to a greatest one of the evaluation values that are obtained in the step of obtaining a preliminary model and an evaluation value as the set of target hyperparameters.

6. The method as claimed in claim 1, the method further comprising steps of:

receiving a test data set that is related to the subject, the test data set including at least one characteristic parameter that is related to one of the physiological conditions and the usage conditions of the subject; and
feeding the test data set into the target model to determine whether or not the subject experienced white coat effect.

7. The method as claimed in claim 1, the method further comprising steps of:
receiving a test data set that is related to the subject, the test data set including at least one characteristic parameter that is related to one of the physiological conditions and the usage conditions of the subject; and
feeding the test data set into the prediction model to obtain the probability of the subject experiencing white coat effect.

8. A non-transitory machine readable storage medium storing program instructions, when being executed by a processor, causing the processor to implement the target model obtained by the method as claimed in claim 1.

9. A computer program product embodied on a non-transitory machine readable storage medium for implementing a method of determining whether a subject experienced white coat effect, the method comprising:
receiving a test data set that is related to the subject, the test data set including at least one characteristic parameter that is related to one of a physiological condition of the subject and a usage condition of a specific drug by the subject; and
feeding the test data set into the target model obtained in claim 1 to determine whether or not the subject experienced white coat effect.

10. A computing device, comprising:
a processor; and
a non-transitory machine readable storage medium that is electrically connected to said processor, and that stores program instructions, when being executed by said processor, causing said processor to
receive a test data set that is related to a subject, the test data set including at least one characteristic parameter that is related to one of a physiological condition of the subject and a usage condition of a specific drug by the subject, and
feed the test data set into the target model obtained in claim 1 to determine whether or not the subject experiences white coat effect.

11. A computing device for establishing a prediction model for predicting probability of a subject experiencing white coat effect, said computing device comprising:
a storage medium configured to store a plurality of training data sets that are respectively related to a plurality of samples and a set of target hyperparameters that is related to a target machine learning algorithm, each of the training data sets including a plurality of characteristic parameters respectively related to a plurality of characteristic conditions of the corresponding one of the samples, and a label that indicates whether the corresponding one of the samples experiences white coat effect, the characteristic parameters including a plurality of physiological parameters that are respectively related to a plurality of physiological conditions of the corresponding one of the samples, and a plurality of drug-usage indicators that respectively indicate usage conditions respectively of a plurality of specific drugs by the corresponding one of the samples; and
a processor electrically connected to said storage medium, and configured to implement a method including steps of
obtaining, by using the target machine learning algorithm and a model-explanation tool based on the training data sets and the set of target hyperparameters, impact values respectively for the characteristic conditions, each of the impact values being related to impact of the characteristic parameters that are respectively included in the training data sets and that are related to the corresponding one of the characteristic conditions on an output of a model that is obtained using the target machine learning algorithm,
for each of the training data sets, selecting one of the characteristic parameters that is related to one of the characteristic conditions corresponding to a greatest one of the impact values from the training data set as a training data subset,
obtaining, based on the training data subsets and the set of target hyperparameters, a candidate model by using the target machine learning algorithm, and an evaluation value related to the candidate model by using a first validation method,
for each of the training data subsets, supplementing the training data subset with one of the characteristic parameters that is related to one of the characteristic conditions corresponding to a greatest one of the impact values among the characteristic parameters that are not included in the training data subset,
obtaining, based on the training data subsets thus supplemented and the set of target hyperparameters, another candidate model by using the target machine learning algorithm, and another evaluation value related to said another candidate model by using the first validation method,
repeating the step of supplementing the training data subset, and the step of obtaining another candidate model and another evaluation value related to said another candidate model based on the training data subsets thus supplemented and the set of target hyperparameters, until the training data subsets, each being supplemented to include all of the characteristic parameters, have been used in the step of obtaining another candidate model and another evaluation value, and
selecting, from among the candidate models that are obtained in the step of obtaining a candidate model and in the step of obtaining another candidate model, one of the candidate models as the prediction model based on the evaluation values respectively related to the candidate models,
wherein said storage medium is further configured to store a plurality of classification thresholds that are related to the target machine learning algorithm,
wherein said processor is configured to implement the method further including steps of
for each of the classification thresholds, obtaining, based on the set of target hyperparameters and the training data subsets that are used to obtain the prediction model, a classification model by using the target machine learning algorithm, and an assessment value related to the classification model by using a third validation method, and
selecting, from among the classification models thus obtained, one of the classification models that corresponds to a greatest one of the assessment values respectively related to the classification models as a target model for determining whether or not the subject experiences white coat effect.

12. The computing device as claimed in claim 11, wherein the model-explanation tool is SHapley Additive explanations (SHAP), and each of the impact values is a Shapley value.

13. The computing device as claimed in claim 11, wherein said processor is configured to implement the method further including steps, for each of the training data sets, of:

determining whether the training data set is missing a physiological parameter related to one of the physiological conditions;

when it is determined that the training data set is missing a physiological parameter, filling the training data set with a predetermined parameter related to the one of the physiological conditions; and performing standardization on each of the physiological parameters.

14. The computing device as claimed in claim 11, wherein said processor is configured to select one of the candidate models that corresponds to a greatest one of the evaluation values as the prediction model.

15. The computing device as claimed in claim 11, wherein:

said storage medium is further configured to store a plurality of sets of candidate hyperparameters that are respectively related to a plurality of candidate machine learning algorithms; and said processor is configured to implement the method further including steps of for each of the sets of candidate hyperparameters, obtaining, based on the training data sets and the set of candidate hyperparameters, a preliminary model by using the corresponding one of the candidate machine learning algorithms, and an evaluation value related to the preliminary model by using a second validation method, and selecting, from among the sets of candidate hyperparameters, one of the sets of candidate hyperparameters that corresponds to a greatest one of the evaluation values that are obtained in the step of obtaining a preliminary model and an evaluation value as the set of target hyperparameters.

16. The computing device as claimed in claim 11, wherein said processor is configured to implement the method further including:

receiving a test data set that is related to the subject, the test data set including at least one characteristic parameter that is related to one of the physiological conditions and the usage conditions of the subject; and feeding the test data set into the target model to determine whether or not the subject experiences white coat effect.

17. The computing device as claimed in claim 11, wherein said processor is configured to implement the method further including:

receiving a test data set that is related to the subject, the test data set including at least one characteristic parameter that is related to one of the physiological conditions and the usage conditions of the subject; and feeding the test data set into the prediction model to obtain the probability of the subject experiencing white coat effect.

* * * * *